United States Patent [19]

Vaughan

[11] Patent Number: 4,504,685

[45] Date of Patent: Mar. 12, 1985

[54] OXYALKYLATION PROCESS

[75] Inventor: Ronald J. Vaughan, Orinda, Calif.

[73] Assignee: Varen Technology, Marshallton, Del.

[21] Appl. No.: 179,520

[22] Filed: Aug. 19, 1980

Related U.S. Application Data

[63] Continuation-in-part of Ser. No. 065,613, Aug. 9, 1979, abandoned, which is a continuation of Ser. No. 904,502, May 10, 1978, abandoned.

[51] Int. Cl.$^3$ .............................................. C07C 41/03
[52] U.S. Cl. ..................................... 568/678; 568/607; 568/608; 568/613; 568/614; 568/618; 568/620; 568/648; 568/649; 568/650; 568/651; 568/672; 568/676; 568/679; 568/867
[58] Field of Search ............... 568/867, 607, 608, 613, 568/614, 618, 620, 645, 649, 650, 651, 672, 676, 679, 678

[56] References Cited

U.S. PATENT DOCUMENTS

| | | | |
|---|---|---|---|
| 2,374,052 | 4/1945 | Spence et al. | 260/464 |
| 2,393,868 | 8/1942 | Toussaint | 568/618 |
| 2,403,672 | 7/1946 | Matuszak | 260/683.2 |
| 2,684,387 | 7/1954 | Young | 568/618 |
| 2,807,651 | 9/1957 | Britton et al. | 568/618 |
| 2,839,588 | 6/1958 | Parker | 260/635 |
| 3,041,317 | 6/1962 | Gibbs | 568/618 |
| 3,282,875 | 11/1966 | Connolly et al. | 568/618 |
| 3,624,053 | 11/1971 | Gibbs | 568/618 |
| 3,629,478 | 8/1969 | Haunschild | 260/677 A |
| 3,634,534 | 8/1969 | Haunschild | 260/677 A |
| 3,784,399 | 1/1974 | Grot | 117/62.1 |
| 3,882,093 | 5/1975 | Cavanaugh et al. | 568/618 |
| 3,954,884 | 5/1976 | Kidwell | 568/618 |
| 3,976,704 | 8/1976 | Vaughan | 260/645 |
| 4,165,440 | 8/1979 | Kim | 568/618 |

OTHER PUBLICATIONS

Innovation, vol. 4, No. 3, (1973), pp. 10–13.
Grot et al., paper, "Perfluorinated Ion Exchange Membranes", presented at 141st *Electrochemical Society* Mtg., Houston, Texas, May 1972.

*Primary Examiner*—James H. Reamer
*Attorney, Agent, or Firm*—Charles J. Tonkin

[57] ABSTRACT

Hydroxyl compounds are oxyalkylated by contacting them with an alkylene oxide, such as ethylene oxide or propylene oxide, in the presence of a perfluorocarbon polymer containing pendant sulfonic acid groups.

8 Claims, No Drawings

4,504,685

OXYALKYLATION PROCESS

This is a continuation-in-part of application Ser. No. 065,613, filed Aug. 9, 1979 now abandoned which in turn is a continuation of application Ser. No. 904,502, filed May 10, 1978 and now abandoned.

FIELD OF THE INVENTION

This invention relates to a process for oxyalkylation of compounds containing at least one hydroxyl group. More particularly, this invention relates to carrying out said oxyalkylation in the presence of a perfluorocarbon polymer containing pendant sulfonic acid groups.

BACKGROUND OF THE INVENTION

The reaction of alkylene oxides, such as ethylene oxide, with alcohols to yield an oxyalkylated alcohol has been known for many years. Commercially, liquid and gaseous sulfonic acids and sulfuric acids have been used as catalysts. The reactors necessary for containing such catalysts are very expensive and in addition, separation of the catalyst from the oxyalkylated product is difficult.

Presumably, sulfonated polymeric substances, such as sulfonated styrene-divinylbenzene polymers or the Amberlyst series of sulfonated polymers (U.S. Pat. No. 3,037,052) would provide a source of sulfonic acid catalytic material that would avoid the problems of the conventional catalysts. However, these catalytic materials have not found wide acceptance in the art because of a number of defects associated with them.

For example, residues from incomplete polymerization, along with initiators for the polymerization, leach out of sulfonated styrene-divinylbenzene resins under any but the mildest reaction conditions. In addition, the sulfonated copolymers in general are fragile, easily crumbled, materials which must be delicately handled. This is a definite drawback when commercial scale operations are involved. A further disadvantage is that the polymers have a low specific activity, so that a relatively large amount of the catalyst must be used.

A final, but very significant, disadvantage of these catalysts is that they cannot be easily regenerated or reused, if the contaminants are not readily removed with warm hydrochloric acid (6N) or its equivalent. Any more-drastic treatment usually degrades the catalyst.

SUMMARY OF THE INVENTION

It has now been found that compounds containing at least one hydroxylic group can be oxyalkylated efficiently and economically with a flexible, easily fabricated catalyst having a high specific activity. This catalyst can be easily regenerated for example, by boiling in concentrated nitric acid, and its use leads to the formation of insignificant amounts of polymeric tars during the course of the reaction. The oxyalkylation reaction according to this invention comprises contacting the hydroxylic compound with an alkylene oxide in the presence of a perfluorocarbon polymer containing pendant sulfonic acid groups.

DETAILED DESCRIPTION OF THE INVENTION

A. The Reactants

The hydroxylic compounds that can be oxyalkylated by the process of this invention include any organic compounds containing one or more hydroxy (—OH) groups. Water is also included within the scope of the term hydroxylic compound. Certain of the hydroxylic compounds contemplated for use within the scope of this invention may also be described by the formulas

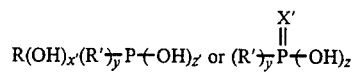

wherein R is hydrogen or hydrocarbyl, R' is hydrocarbyl, hydrocarbyl —X'—, or hydrogen, X' is oxygn or sulfur, x is an integer, preferably of 1 to 6, with the proviso that when R is hydrogen, x is one, z is an integer from 1 to 3, and y is 3-z. Of particular interest are those hydroxylic compounds wherein R is hydrogen, alkyl of 1–20 carbon atoms, phenyl, alkylphenyl of 7 to 30 carbon atoms, hydroxyalkyl of 2 to 20 carbons, or hydrocarbyloxyalkyl of the formula hydrocarbyl $-[O-alkyl]_g-$ where the hydrocarbyl group contains 1–20 carbon atoms, alkyl is ethylene or propylene and g is at least one.

The hydrocarbyl portion of the hydroxylic compound may be aliphatic, cycloaliphatic, aromatic, or a combination of two or more types of hydrocarbon groups. The hydrocarbyl radical may contain any substituents that do not react with the alkylene oxide under the reaction conditions of the instant invention more readily than does a hydroxyl group. The substituents on the hydrocarbyl group also should not be of a type that might poison the catalyst. Substituent groups that should be avoided can be readily determined by one skilled in the art. Typical of such groups are amino, mercapto, and metal carboxylate. Substituent groups that may be present on the hydrocarbyl portion of the hydroxylic compound without affecting the oxyalkylation reaction include nitro, hydrocarbyloxy, halo, phosphonate, phosphate,

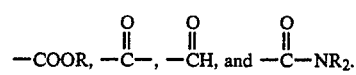

The R group is preferably a straight or branched-chain alkyl of 1 to 20 carbon atoms, H or phenyl.

Particularly preferred hydroxylic compounds are water, methanol, ethanol, 1-dodecanol, 1-butanol, isobutanol, ethylene glycol, glycerol, pentaerythritol, sorbitol, phenol, and alkylated phenols.

The alkylene oxides intended for use within the scope of this invention fall within the general formula

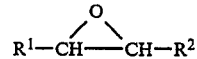

wherein each of $R^1$ and $R^2$ is hydrocarbyl of 1 to 20 carbon atoms or $R^1$ and $R^2$ together with the two carbon atoms form a five- or six-membered cycloaliphatic ring.

Typical alkylene oxides contemplated for use within the scope of this invention are ethylene oxide, propylene oxide, 1,2-butylene oxide, 2,3-butylene oxide, 1,2-pentylene oxide, 2,3-pentylene oxide, 1,2-hexylene oxide, 3-methyl-1,2-pentylene oxide, 2,3-octyleneoxide, 4-methyl-2,3-octylene oxide, 4-methyl-1,2-hexylene oxide, and 3-methyl-1,2-butylene oxide. Because of their commercial availability, ethylene oxide and propylene oxide are preferred. Ethylene oxide is particularly preferred.

B. The Catalyst

The catalyst used for the oxyalkylation reaction of this invention is a perfluorocarbon polymer containing pendant sulfonic acid groups. A preferred catalyst is the perfluorocarbon polymer having the repeating structure

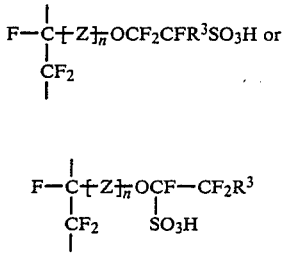

wherein n is 0, 1 or 2, $R^3$ is —F or perfluoroalkyl of 1 to 10 carbon atoms, Z is —O—$CF_2$—$(CF_2)_m$, —$OCF_2$—CFY— or —$OCFYCF_2$— where m is an integer from 1 to 9, and Y is —F or trifluoromethyl.

Useful perfluorocarbon polymers and their preparation are described in U.S. Pat. Nos. 3,041,317, 3,282,875, 3,624,053 and 3,882,093, the disclosures of which are hereby incorporated by reference.

Catalysts of the above-noted structure typically have a molecular weight of between 1,000 and 500,000 daltons.

Polymer catalysts of the above-noted structure can be prepared in various ways. One method, disclosed in Connolly et al, U.S. Pat. No. 3,282,875, and Cavanaugh et al, U.S. Pat. No. 3,882,093, comprises polymerizing vinyl ethers of the formula:

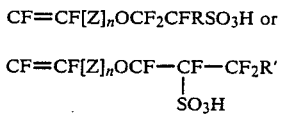

in a perfluorocarbon solvent using a perfluorinated-free radical initiator. Since the vinyl ethers are liquid at reaction conditions, it is further possible to polymerize and copolymerize the vinyl ethers in bulk without the use of a solvent. Polymerization temperatures vary from −50° to +200° C. depending on the initiator used. This special method of operation is claimed in copending application, Ser. No. 306,482, filed Sept. 28, 1981 now U.S. Pat. No. 4,409,403. Pressure is not critical and is generally employed to control the ratio of the gaseous comonomer to the fluorocarbon vinyl ether. Suitable fluorocarbon solvents are known in the art and are generally perfluoroalkanes or perfluorocycloalkanes, such as perfluoroheptane or perfluorodimethylcyclobutane. Similarly, perfluorinated initiators are known in the art and include perfluoroperoxides and nitrogen fluorides. It is also possible to polymerize the vinyl ethers of the above structures in an aqueous medium using a peroxide or a redox initiator. The polymerization methods employed correspond to those established in the art for the polymerization of tetrafluoroethylene in aqueous media.

It is also possible to prepare catalysts for the present invention by copolymerizing the vinyl ethers of the above structure with tetrafluoroethylene and/or perfluoroalphaolefins. A preferred copolymer prepared by polymerizing perfluoroethylene with a perfluorovinyl ether containing sulfonic acid groups would have the following structure:

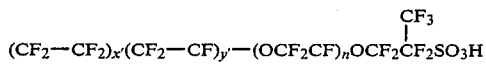

wherein n is 1 or 2 and the ratio of x' over y' varies from about 2 to 50. Polymers of this structure are available commercially under the tradename of NAFION resin (E. I. duPont). Catalysts of this structure offer the advantages of high concentrations of accessible acid groups in a solid phase. As indicated by the x'/y' ratio above, the equivalent weight (expressed as grams polymer per sulfonic acid group) can range from 644 or 810 upwards depending on whether n=2 or 1.

W. G. F. Grot et al. in "Perfluorinated Ion Exchange Membranes", a paper presented at the May 1972 National Meeting of the Electrochemical Society, plots water absorption for the perfluorinated ether polymer sulfonic acid against equivalent weights over the range 800 to 2000; as indicated thereby the more active polymers have equivalent weights somewhat below 2000. Generally preferred are equivalent weights of 900 to 1700 and more preferably below 1500. The equivalent weight of the catalyst used in the Examples was 1200.

The catalyst may be used in the process of this invention in a variety of physical forms, that is, it may be fabricated into sheets, hollow tubes, granules having a particle size of from 6 mesh to less than 400 mesh, fibers, and the like. The catalyst may be used alone or it may be supported, for example, by coating it onto a metal or combining with other common catalyst supports as is well known in the art. The catalyst is insoluble in and inert to deactivation by the reaction mixtures and conditions used in the process of this invention. For this reason, the catalyst is easy to separate from the reactants and products. Furthermore, the life of the catalyst is considerably longer than is the life of conventional sulfonated resin catalysts.

In order for the resins of this invention to have catalytic activity of a degree sufficient to make them useful for the process of this invention, it is necessary that they be activated by (1) contacting the resin with a strong acid having a pKa less than zero at elevated temperature, for example, contacting with 70% nitric acid at 110° C., and (2) washing the resin with water until the wash water is neutral. When water is not the reactant being oxyalkylated, it is necessary to either dry the catalyst to constant weight to remove the water or to displace the water with the hydroxylic reactant to be used prior to the introduction of the alkylene oxide.

The catalyst may be cleaned after use using the same procedure described above. The cleaning process can be used to remove any residual tars that form during the reaction, to restore any lost degree of catalytic activity, or to remove residual hydroxylic reactants when the catalyst is to be used with a different reactant.

C. The Reaction Conditions

The hydroxylic compound to be oxyalkylated using the process of this invention is contacted with an alkylene oxide in the presence of a perfluorocarbon polymer having pendant sulfonic acid groups. The temperature and pressure of the reaction zone are maintained so as to maximize the production of the desired products. Usually, the product of choice is the one having only one oxyalkyl group per hydroxylic group in the hydroxylic compound; however, in certain situations it will be desirable to form a polyoxyalkylene group on the hydroxylic compound. The molar ratios of reactants necessary to achieve the desired product will be readily apparent to one skilled in the art and will vary with the product desired. Thus, for example, the mol ratios for water and ethylene oxide generally used heretofore are from about 1:1 up to 50:1 or more; commonly used are mol ratios of 5:1 or 10:1 to 30:1 (i.e., weight ratios of about 2:1 or 4:1 to 12:1). Thus, a generally preferred range for initial weight ratios can be from 3:1 to 15:1.

Pressure and temperature are likewise adjusted to achieve the desired product. Again, determination of the desirable ranges for each set of reactants is well within the skill of the art. Usually the temperature is maintained between 0° C. and 150° C. Generally, the temperature initially is at least 50° C. (note the examples following) and with the preferred procedure at reflux (i.e., 100° C. when using water). Thus, a generally preferred temperature range is 50° to about 100° C. or up to somewhat higher such as 110° or 125° C. The reactions contemplated for use in the process of this invention ordinarily are most readily carried out at atmospheric pressure. However, higher or lower pressures may be employed if desired.

When a mono-oxyalkylated hydroxylic compound is desired, it can be prepared with up to 99 percent or greater selectivity using a preferred method of operation provided as part of this invention. This preferred method is not limited to the use of perfluorocarbon polymers having pendant sulfonic acid groups. It is equally applicable for use with any insoluble solid acidic catalyst, that is, one which is not soluble or only soluble to a negligible extent in the reactants or products under the process conditions described herein. However, the perfluorocarbon polymers are preferred because of their above-described advantages as oxyalkylation catalysts.

The operation of this preferred steady-state method can be described as follows. The hydroxylic compound is heated to vaporization in a reflux zone. This vaporized mixture then passes through the catalyst zone to a condensing zone where the vaporized mixture becomes liquid and returns to the catalyst zone where it contacts both vaporized hydroxylic compound and the solid acidic catalyst. The alkylene oxide is introduced into the reflux zone, the condensing zone, or the catalyst zone. It is necessary for the reaction conditions to be such that the alkylene oxide is present to some extent in the catalyst zone.

When the hydroxylic compound and the alkylene oxide come into contact in the catalyst zone, a monoalkylated hydroxylic compound is formed. The monooxyalkylated derivative then returns (as a mixture with unreacted hydroxylic compound) to the reflux zone where it is recovered by fractionation of the mixture of hydroxylic compound and mono-oxyalkylated derivative thereof (the unreacted hydroxylic compound being sent overhead to the catalyst zone).

A mono-oxyalkylated hydroxylic compound essentially free of polyoxyalkylated derivatives is continuously prepared by the above method. The process also minimizes the amount of energy needed to carry it out, because the heat of reaction generated by oxyalkylation is removed in the condensation zone which is preferably separate from the catalyst zone. Thus, heat of reaction is converted to heat of vaporization in the catalyst zone, thereby maintaining microscopic temperature control at the catalyst sites. Heat of reaction is removed in the condensation zone, allowing great flexibility in construction and ease of maintenance of the reactor being used.

The preferred mode of operation is especially suitable in instances wherein the oxyalkylated derivative will further react with the alkylene oxide at a greater rate than the hydroxylic compound. The selectivity for the mono-oxyalkylated derivative may be improved by means of the process of the instant invention. In this method the oxyalkylated derivative must have a higher boiling point than the hydroxylic compound. Furthermore, the alkylene oxide preferably has a much lower boiling point, preferably at least 10° C. lower, than either the hydroxylic compound or its oxyalkylated derivative so that it will not be returned in its unreacted form to the refluxing mixture. In general, any difference in boiling point of, for example, at least 5° C. between the oxyalkylated derivative and the hydroxylic compound is suitable for carrying out this preferred process. Preferably, the oxyalkylated derivative will have a boiling point at least 10° C. greater than the boiling point of the hydroxylic compound.

Variations of the above process will be readily apparent to one skilled in the art. For example, the hydroxylic compound may be condensed in the same zone where the solid acid catalyst is present or it may be condensed at a point above the catalyst and fed by gravity into the catalyst zones.

Apparatus used to carry out the above process may be of various designs. One such type is described below and designated as a reactor-fractionator. The following examples are presented for the purpose of illustrating the invention and should not in any way be construed as limiting the invention being claimed herein.

EXAMPLE 1

Reaction of Ethylene Oxide With Ethanol in a Flowing Tube Reactor

Nafion ® fibers (0.006" diameter, 66 fibers, 50 inches long tied at the midpoint, 6.71 g catalyst weight) were fitted as a parallel bundle inside a polypropylene tube (3'×¼" O.D.×0.040" wall). The catalyst was prepared by heating with 70% nitric acid at 80°–100° C., then equilibrated with absolute ethanol under flow at 53° C. before introduction of ethylene oxide at a tee prior to the inlet fittings (the tube was suspended in a forced-fan oven maintained by a thermistor temperature controller). Samples were collected in a graduated cylinder and analyzed by gas chromatography with 2-methoxyethanol as internal standard. The results are presented in Table I.

TABLE I

| Sample | Volume in ml | Ethylene Oxide, ml/min | Ethanol ml/min | $H_3CCH_2OCH_2CH_2OH$ % weight/volume | $H_3CCH_2O(CH_2CH_2O)_2H$ % weight/volume |
| --- | --- | --- | --- | --- | --- |
| 1  | 20  | 3–3.5 | 0.56 | 0.6  | —  |
| 2  | 10  | 3–3.5 | 0.56 | 4.2  | —  |
| 3  | 15  | 8     | 0.56 | —    | —  |
| 4  | 7   | 8     | 0.56 | 6.3  | —  |
| 5  | 17  | 14    | 0.56 | —    | —  |
| 6  | 6   | 14    | 0.56 | 11.9 | 1.5 |
| 7  | 17  | 25    | 0.56 | —    | —  |
| 8  | 11  | 22    | 0.56 | 17.5 | 3.3 |
| 9  | 20  | 35–37 | 0.56 | —    | —  |
| 10 | 10  | 34    | 0.56 | 23.8 | 5.3 |
| 11 | 23  | 45    | 0.56 | —    | —  |
| 12 | 13  | 44    | 0.56 | 29.6 | 7.7 |
| 13 | 22  | 58    | 0.56 | —    | —  |
| 14 | 12  | 57    | 0.56 | 30.1 | 9.6 |
| 15 | 21  | 72–75 | 0.56 | —    | —  |
| 16 | 8   | 72–75 | 0.56 | 37.9 | 15.5 |
| 17 | 26  | 35    | 0.28 | —    | —  |
| 18 | 5   | 35    | 0.28 | 30.2 | 12.3 |
| 19 | 20  | 47    | 0.28 | —    | —  |
| 20 | 13  | 42–43 | 0.28 | 29.6 | 1 (integrator off scale) |
| 21 | 18  | 85    | 0.28 | —    | —  |
| 22 | 10  | 85    | 0.28 | 20.5 | 8.8 |
| 23 | <2  | 85    | 0.28 | 24.7 | 8.8 |

EXAMPLE 2

Reaction of Ethylene Oxide With Methanol in a Flowing Tube Reactor

The reactor of Example 1 was cycled in the usual manner and equilibrated with methanol under flow (0.50 ml/min at 40° C.). Ethylene oxide was introduced at atmospheric pressure through a flowmeter to a tee at the entrance of the reactor. The temperature was raised to 51° C. where reaction visibly proceeded readily. At higher flow rates of ethylene oxide, some gas was seen to escape from the outlet of the reactor indicating incomplete absorption/reaction. Portions of collected samples were mixed with an equal volume of 10% w/v 2-ethoxyethanol in ethanol for analysis by gas chromatography. The results are shown in Table II.

TABLE II

| Sample | Ethylene Oxide ml/min | T (°C.) | $CH_3OCH_2CH_2OH$ % weight/volume | $CH_3O(CH_2CH_2O)_2H$ % weight/volume |
| --- | --- | --- | --- | --- |
| 1 | 2.5 | 40 | 0    | 0 |
| 2 | 2.5 | 51 | 2.1  | trace |
| 3 | 6   | 51 | 4.5  | trace |
| 4 | 12  | 51 | 8.3  | trace |
| 5 | 25  | 51 | 15.3 | 1.3 |
| 6 | 50  | 51 | 21.1 | 3.8 |

EXAMPLE 3

Reaction of Ethylene Oxide With Water in Integrated Reactor-Fractionator

The bulbs of an eight-bulb Allihn condenser evacuated in the outer jacket were packed loosely with wads of wet Nafion fibers (9.8 g total, wet) which had been converted to the hydrogen form by treating at 80°–100° C. with 70% nitric acid and washing with water until the wash water was neutral. This catalyst section was fitted atop a reflux-fractionator apparatus which consisted of (in ascending order): a 500 ml r.b. flask with thermometer side arm, a 30×2 cm vigreaux column, insulated, and a short connecting tube with a side arm. A reflux condenser and bubbler were connected to the top of the catalyst section to observe any exit gas flow and to return reactants to the catalyst section. The flask was charged with 100 ml of water, 50 mg of $NaHCO_3$, and a few boiling chips. Reflux was established through the catalyst section, then ethylene oxide was introduced through the side arm into the tube below the catalyst section. Flow was maintained at 30 ml/min for 18 hours, then increased to 60 ml/min for 2 hours, and then to 80 ml/min for 7.5 hours. The ethylene oxide flow was terminated overnight while reflux was maintained. The ethylene oxide flow was resumed at 80 ml/min for an additional 8 hours; the reaction was terminated at a boiling temperature of 197° C. (730 mm) of the flask contents. Most of the pot contents (340.0 g) were distilled through a 30×1 cm vigreaux column to yield the results shown in Table IIIA.

TABLE IIIA

| | Product of Example 3A | | | | |
| --- | --- | --- | --- | --- | --- |
| Fraction | $T_{head}$ (°C.) | $T_{pot}$ (°C.) | wt (g) | % | Remarks |
| 1 | 99–195.5   | 193–202 | 3.4   | 1.0  | |
| 2 | 195.5–201  | 202–245 | 230.0 | 68.0 | $HOCH_2CH_2OH$ |
| 3 | 201–242    | 245–255 | 7.6   | 2.2  | |
| 4 | 242–247.5  | 255–275 | 40.5  | 12.0 | $HOCH_2CH_2OCH_2CH_2OH$ |
| 5 | 247.5–256  | 275–    | 15.6  | 4.6  | |
| Residue | | | 41.1 | 2.1 | |

The high oligomer (n>1) content of the distillate in IIIA prompted a brief investigation of the effect of ethylene oxide flow rate and efficiency of the fractionating column.

After removal of the pot contents of the reactor-fractionator from the experiment above, the catalyst section was washed by refluxing with fresh water in the pot for 1 hour; the pot contents were removed and replaced with 100 ml of fresh distilled water containing 50 mg of $NaHCO_3$. Reflux was again established and ethylene oxide was introduced at a flow rate of 16 ml/min for 150 hours. The boiling temperature of the pot contents was then 183° C. (730 mm Hg). A small sample was removed for analysis and the remainder of the pot contents (314.3 g) was distilled (730 mm Hg) through a 1×30 cm vigreaux column to yield the results shown in Table IIIB.

TABLE IIIB

| Fraction | $T_{head}$ (°C.) | $T_{pot}$ (°C.) | wt (g) | % | Remarks |
|---|---|---|---|---|---|
| 1 | 98–186 | 156–195 | 16.1 | 5.1 | |
| 2 | 186–193 | 195–197 | 6.3 | 2.0 | |
| 3 | 193–200 | 197–218 | 254.5 | 81.1 | $HOCH_2CH_2OH$ |
| 4 | 200–241 | 218–248 | 13.4 | 4.2 | |
| 5 | 241–253 | 248–305 | 16.3 | 5.2 | $HOCH_2CH_2OCH_2CH_2OH$ |
| 6 | 253–266 | 305–320 | 2.1 | 0.7 | |
| Residue | | | 4.7 | 1.5 | |

The catalyst section was again washed as above; the vigreaux column used in the reactor-fractionator was replaced by a 30×2 cm vacuum-jacketed fractionating column packed with stainless steel helices. Reflux was established using 50 ml of distilled water and 50 mg of $NaHCO_3$ in the pot. Ethylene oxide was introduced at a flow rate of 10–14 ml/min. and continued until the pot contents had reached a boiling temperature of 195° C. (730 mm Hg). Gas chromatography of the neat pot contents (on a Carbowax 20M column) revealed only traces of diethylene glycol; the sole organic peak (>99%) was ethylene glycol.

Control (without catalyst)

The reactor-fractionator above was charged with 100 ml of water, 50 mg $NaHCO_3$ and boiling chips. The catalyst section was replaced by an identical Allihn condenser (evacuated outer jacket) without the Nafion ® fiber catalyst. Reflux was established through this section, then ethylene oxide was introduced at 15 ml/min. Although little gas was observed escaping through the bubbler initially, rapid gas flow was established within an hour. Ethylene oxide flow was continued for 6 hours. The contents of the pot showed a weight loss of 2.1 g and only minute traces of organic materials, primarily ethylene glycol, on gas chromatography.

EXAMPLE 4

Reaction of Ethylene Oxide With Methanol in Integrated Reactor-Fractionator

A bundle of parallel Nafion ® fibers (0.006" diameter, 45 fibers 180 cm long, suspended from their midpoint, 4.48 g total weight) was fitted inside a straight tube condenser and the outer jacket was evacuated. The catalyst was prepared as described in Example 1 and the assembled reactor-fractionator (with the stainless-steel helice-packed fractionator) brought up to reflux with methanol to equilibrate the catalyst. The reactor was cooled and allowed to drain; the pot contents were replaced with 80.1 g of fresh methanol containing 50 mg of $NaCHO_3$. After establishing reflux through the catalyst section, ethylene oxide was introduced at 100–200 ml/min. over a period of 8.24 hours. When the boiling temperature of the pot contents reached 126.5° (730 mm Hg) the reaction was halted and the reactor allowed to drain down. A portion (202.1 g) of the pot contents (203.6 g) was distilled (730 mm Hg) through a 30×1 cm vacuum-jacketed vigreaux column to yield the results shown in Table IVA.

TABLE IVA

| Fraction | $T_{head}$ (°C.) | $T_{pot}$ (°C.) | net wt (g) | % of product | Remarks |
|---|---|---|---|---|---|
| 1 | 65–122 | 124–125 | 7.2 | 3.6 | |
| 2 | 122–124.5 | 125–198 | 173.5 | 85.8 | $CH_3OCH_2CH_2OH$ |
| 3 | 124.5–191 | 198–199 | 0.8 | 0.4 | |
| 4 | 191–194 | 199–262 | 14.1 | 7.0 | $CH_3O(CH_2CH_2O)_2H$ |
| Residue | | | 5.4 | 2.5 | |

A second preparation using an ethylene oxide flow of 15–20 ml/min. required a correspondingly longer time (46 hours) to complete the reaction; gas chromatographic analysis on a Carbowax 20M column showed the only organic product to be 2-methoxyethanol with a trace of methanol remaining.

EXAMPLE 5

Reaction of Ethylene Oxide With Ethanol in the Integrated Reactor-Fractionator

The catalyst section and reactor-fractionator were prepared as in Example 4 and equilibrated with ethanol under reflux. The pot contents were replaced with 70.4 g of fresh absolute ethanol and reflux was established through the catalyst section. Ethylene oxide was introduced at a flow rate of 15–25 ml/min. for a period of 32 hours; the boiling temperature of the pot contents rose to 132° C. (730 mm Hg). A small sample of the pot contents (133.5 g total) was removed for analysis; the remainder (132.1 g) was distilled (730 mm) through a 30×1 cm vacuum-jacketed vigreaux column to yield the results shown in Table V.

TABLE V

| Fraction | $T_{head}$ (°C.) | $T_{pot}$ (°C.) | net wt (g) | % of product | Remarks |
| --- | --- | --- | --- | --- | --- |
| 1 | 76.5–126 | 117–135 | 11.0 | 8.3 | |
| 2 | 126–133 | 135–136 | 2.4 | 1.8 | |
| 3 | 133–136 | 136–195 | 108.1 | 82.4 | $CH_3CH_2OCH_2CH_2OH$ |
| 4 | 136–189 | 195–279 | 5.5 | 4.2 | |
| Pot Residue | | | 1.0 | 2.8 | |

In the foregoing examples, the mol ratio of the hydroxy compound to ethylene oxide ranged from about 2 to 100. Thus, for example, the mol ratios for samples 6, 12 and 16 in Table I were approximately 13:1, 4:1 and 2:1, respectively; and for samples 4, 5 and 6 in Table II were approximately 23:1, 11:1 and 6:1, respectively. In Example 3 the mol ratio when starting with a nominal flow rate of 80 ml/min. for ethylene oxide was estimated at 25:1 at minimum refux conditions up to 50:1 for average reflux conditions, the mol ratio decreasing as the reaction with water nears completion.

As illustrated, the present process using a sulfonated perfluorocarbon ether is decidedly superior to other processes, which are compared as follows: Reed et al in an article in Industrial and Engineering Chemistry, Vol. 48, pages 205–208 (February, 1956) proposed a process for hydrating ethylene oxide using certain acidic ion exchange resins. For example, the conversion rate at 108° C. (226° F.) in Example 12 (assuming a maximum of 1 gm. catalyst per milliliter of bed) was only about 0.00015 moles ethylene oxide per minute per gram of catalyst (which is a measure of the turnover rate of ethylene oxode at the catalyst site, i.e., a measure of catalyst efficiency). For all of Reed et al's data, the best observed run is Run 10A which gives an efficiency of 0.00033 moles of ethylene oxide per minute per gram of catalyst. Also, Othmer et al in an article in Industrial and Engineering Chemistry, Vol. 50, pages 1235–1244 (September, 1958) presents data on hydration of ethylene oxide using an Amberlite ion exchange resin as catalyst and Othmer et al's best result comparable to Example 1 hereinabove at about the same temperature (50° C. versus 50° C.), namely, Column 8 of Table V (on page 1240 of Othmer et al), gave an efficiency of 0.000153 moles of glycol per minute per gram of resin. This compares to an obtainable efficiency of the present sulfonated fluorocarbon ether polymer of 0.00055 moles per minutes per gram of catalyst of monoethoxylated ethanol and diethoxylated ethanol in Sample 16 of Table I above. Othmer et al's results in Col. 1, Col. 2 and Col. 7 of their Table V—all at 80° C.—a much higher temperature at which greater efficiencies would be expected—, gave 0.000217, 0.000095 and 0.000447 moles per minute per gram, all of which are lower than noted above with the sulfonated fluorocarbon ether polymer at the lower temperature of 53° C. Japanese Pat. No. 38-4858 describes the reaction of methanol and 2 moles of ethylene oxide at a 10:1 molar ratio at 65° C. with a styrene, strongly acidic cation exchange resin. At a reaction time of 60 minutes and a yield of 34.3%, the catalyst efficiency is 0.000082. This is only 15% of the efficiency obtainable for the sulfonated fluorocarbon ether catalyst as noted above, even though the temperature used in the Japanese patent is substantially higher where the efficiency would be expected to be greater. These comparisons illustrate that the present invention is decidedly superior.

I claim:

1. In the process for the oxyalkylation of a hydroxylic compound by contacting it with an alkylene oxide, the improvement comprising contacting said hydroxylic compound and said alkylene oxide in the presence of a perfluorocarbon polymer containing pendant sulfonic acid groups wherein said hydroxylic compound is water, an aliphatic alcohol, an aromatic alcohol, an oxyalkylated aliphatic alcohol, or an oxyalkylated aromatic alcohol, and said perfluorocarbon polymer contains the repeating structure

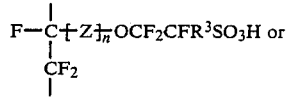

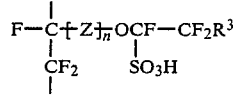

2. The process of claim 1 where said hydroxylic compound has the formula ROH where R is hydrogen, alkyl of 1 to 20 carbon atoms, phenyl, alkylphenyl of 7 to 30 carbon atoms, hydroxyalkyl of 2 to 20 carbon atoms or hydrocarbyloxy alkyl of the formula hydrocarbyl $-(O-(CH_2)_q)_p-$ where the hydrocarbyl group contains 1 to 20 carbon atoms, q is 2 or 3, and p is an integer of at least 1.

3. The process of claim 2 where said alkylene oxide is ethylene oxide, said perfluorocarbon polymer is a copolymer of tetrafluoroethylene and a perfluorovinyl ether containing pendant sulfonic and groups.

4. The process of claim 3 wherein said hydroxylic compound is water, ethanol or methanol.

5. In the process of adding water to ethylene oxide to produce ethylene glycol by contacting ethylene oxide with water in the presence of an acid ion exchange resin at an initial water to ethylene oxide weight ratio varying from about 1:1 to about 50:1 or more and a temperature between about 50° C. to about 110° C., the improvement which comprises using as the acid ion exchange resin a resin selected from the group consisting of resins having the formulas:

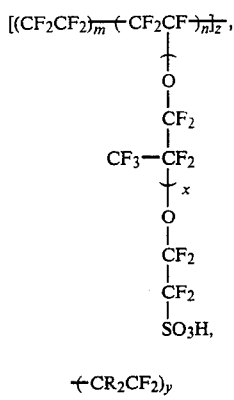

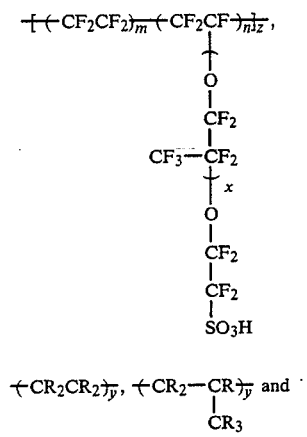

where n, m, x, and z are integers such that the equivalent weight is less than 2000 and where R is individually a hydrogen, a fluorine and a —SO₃H group, at least some of the carbons attached to greater than one R have both a fluorine and a —SO₃H group attached thereto.

6. The process of claim 5 wherein the initial weight ratio of water to ethylene oxide ranges from about 3:1 to about 15:1.

7. In the process for oxyalkylation of a hydroxylic compound by contacting alkylene oxide with said hydroxylic compound in the presence of an acid ion exchange resin, and wherein said hydroxylic compound is water, an aliphatic alcohol, an aromatic alcohol, an oxyalkylated aliphatic alcohol, or an oxyalkylated aromatic alcohol, the improvement which comprises using as the acid ion exchange resins a resin selected from the group consisting of resins having the formulas:

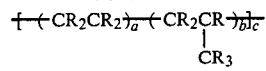

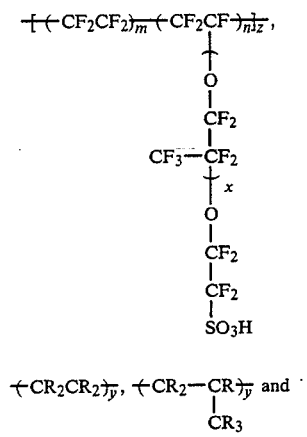

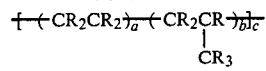

-continued

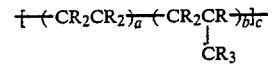

where n, m, x and z are integers such that the equivalent weight is less than 2000 and where R is individually a hydrogen, a fluorine and a —SO₃H group, at least some of the carbons attached to greater than one R have both a fluorine and a —SO₃H group attached thereto and where a, b, and c are integers the sum of which are such that the equivalent weight is less than 2000.

8. In the process for oxyalkylation of a hydroxylic compound by contacting alkylene oxide with said hydroxylic compound in the presence of an acid ion exchange resin at an initial hydroxylic compound to alkylene oxide weight ratio of at least 1:1 and a temperature between about 50° C. to about 150° C., and wherein said hydroxylic compound is water, an aliphatic alcohol, an aromatic alcohol, an oxyalkylated aliphatic alcohol, or an oxyalkylated aromatic alcohol, the improvement which comprises using as the acid ion exchange resins a resin selected from the group consisting of resins having the formulas:

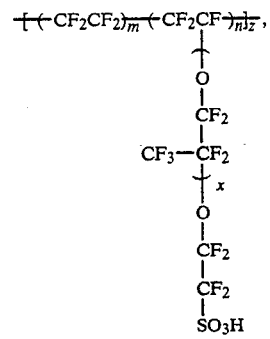

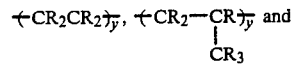

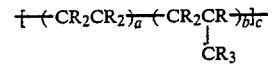

where n, m, x and z are integers such that the equivalent weight is less than 2000 and where R is individually a hydrogen, fluorine and a —SO₃H group, at least some of the carbons attached to greater than one R have both a fluorine and a —SO₃H group attached thereto and where a, b, and c are integers the sum of which are such that the equivalent weight is less than 2000.

* * * * *